United States Patent
Torii et al.

(10) Patent No.: US 6,339,152 B1
(45) Date of Patent: Jan. 15, 2002

(54) PROCESS FOR PRODUCING EXO-METHYLENEPENAM COMPOUNDS

(75) Inventors: Sigeru Torii, Okayama-ken; Hideo Tanaka, Okayama; Yutaka Kameyama; Yoshihisa Tokumaru, both of Tokushima, all of (JP)

(73) Assignee: Otsuka Kagaku Kabushiki Kaisha, Osaka (JP)

( * ) Notice: Subject to any disclaimer, the term of this patent is extended or adjusted under 35 U.S.C. 154(b) by 0 days.

(21) Appl. No.: 09/380,582

(22) PCT Filed: Mar. 5, 1998

(86) PCT No.: PCT/JP98/00903

§ 371 Date: Sep. 7, 1999

§ 102(e) Date: Sep. 7, 1999

(87) PCT Pub. No.: WO98/39336

PCT Pub. Date: Sep. 11, 1998

(30) Foreign Application Priority Data

Mar. 5, 1997 (JP) ............................................. 9-069215

(51) Int. Cl.[7] ..................... C07D 499/87; C07D 499/46
(52) U.S. Cl. ..................................................... 540/310
(58) Field of Search .......................................... 540/310

(56) References Cited

FOREIGN PATENT DOCUMENTS

JP          54-103385          8/1979

OTHER PUBLICATIONS

Hideo Tanaka et al, Chemistry Letters (1997), No. 12, pp. 1221–1222.
Hideo Tanaka et al, The Journal of Organic Chemistry (1997), vol. 62, No. 11, pp. 3610–3617.
Hideo Tanaka et al, Chemistry Express (1992), vol. 7, No. 11, pp. 885–888.
Patent Abstracts of Japan, for JP 54–103385.

*Primary Examiner*—Mark L. Berch
(74) *Attorney, Agent, or Firm*—Arent Fox Kintner Plotkin & Kahn, PLLC

(57) ABSTRACT

The present invention is directed to a process for preparing an exo-methylenepenam compound wherein a cephem compound is reduced with a metal having a standard oxidation-reduction potential of up to −0.3 (V/SCE) in an amount of at least one mole per mole of the cephem compound and with a metal compound having a higher standard oxidation reduction potential than the metal and in an amount of 0.001 to 10 moles per mole of the cephem compound and wherein X is a halogen atom, lower alkylsulfonyloxy, trifluoromethanesulfonyloxy, trichloromethanesulfonyloxy, arylsulfonyloxy, toluenesulfonyloxy, or halogenated sulfonyloxy (1)

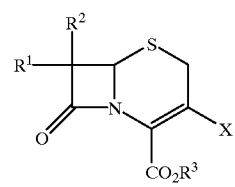

(2)

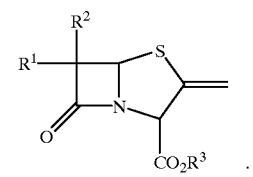

4 Claims, No Drawings

PROCESS FOR PRODUCING EXO-METHYLENEPENAM COMPOUNDS

TECHNICAL FIELD

The exo-methylenepenam compound of the present invention is an important intermediate for synthesizing, for example, a β-lactamase inhibitor (Bawldwin et al, J. Chem. Soc., Chem. Commun., 1987, 81, S. Torii et al., Antibit. Chem. Lett., 1993, 3, 2253).

BACKGROUND ART

A process is already known for preparing the exo-methylenepenam compound of the invention which is represented by the general formula (2), by the decarboxylation Pummerer-type rearrangement reaction of penam-2-carboxylic acid derived from penicillin as illustrated in Diagram (A) (Bawldwin et al., J. Chem. Soc., Chem. Commun., 1987, 81), whereas this process comprises as many as eight reaction steps, and is as low as up to 6% in overall yield and by no means feasible.

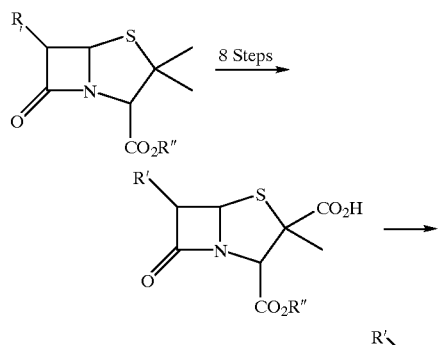

Diagram (A)

(wherein R'=PhOCH$_2$CONH, R''=CH$_2$C$_6$H$_4$NO$_2$-p)

Also known are a synthesis process wherein an allenyl β-lactam compound obtained from penicillin is subjected to acid hydrolysis, followed by intramolecular cyclization (S. Torii et al., Tetrahedron Lett., 1991, 32, 7445) as shown in Diagram (B), and a synthesis process wherein an allenyl β-lactam compound is subjected to a reductive cyclization reaction (S. Torii et al., Synlett., 1992, 878, S. Torii et al., Chemistry Express, 1992, 7, 885, J. Chem. Soc., Chem. Commun., 1992, 1793). These processes nevertheless have various problems such as cumbersomeness of the reaction procedure for industrial operation since the reaction is conducted via an unstable allene compound as an intermediate.

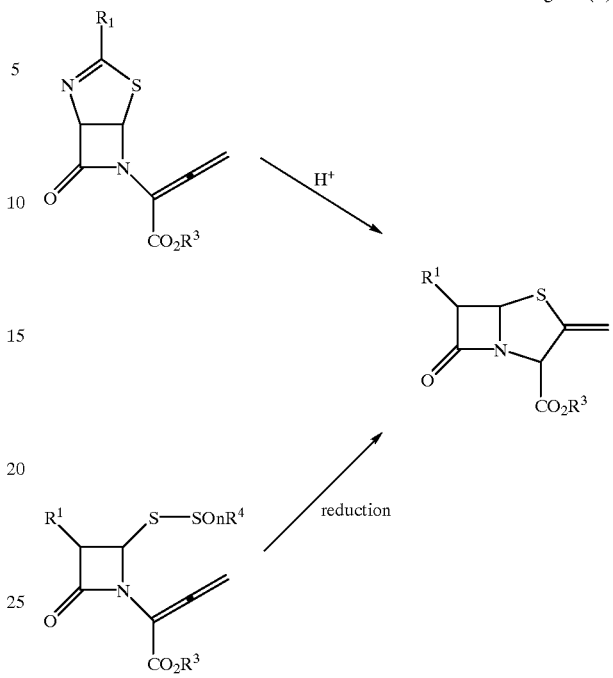

Diagram (B)

(wherein $R^1$~$R^3$ are same as above, $R^4$ is aryl group which may have a substituent)

Further known is a synthesis process wherein a halogenated β-lactam compound derived from penicillin is subjected to reduction for cyclization (Chemistry Letters, 1995, 709, JP-8-245,629 A). However, this process comprises many reaction steps compared with other processes because of use of the halogenated β-lactam compound as an intermediate. Thus, reactions which are more practical are desired.

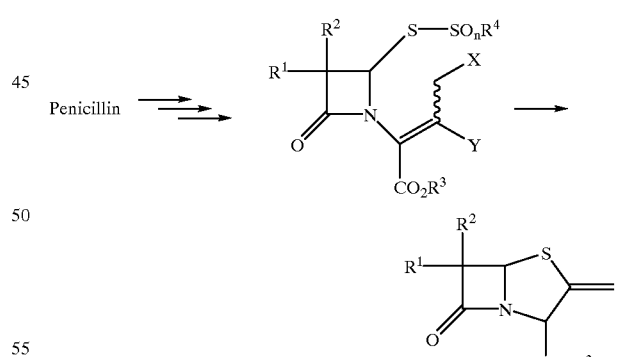

Diagram (C)

(wherein $R^1$~$R^4$ are same as above)

An object of the invention is to provide a process adapted to produce an exo-methylenepenam compound of the formula (2) from the cephem compound of the formula (1) in a high yield with a high purity through a safe and simplified procedure by developing a novel metal reduction system.

DISCLOSURE OF THE INVENTION

The present invention further provides a process for preparing an exo-methylenepenam compound represented by the formula (2) wherein cephem compound represented by the formula (1) is reduced with a metal having a standard oxidation-reduction potential of up to −0.3 (V/SCE) in an amount of at least one mole per mole of the cephem compound and with a metal compound having a higher standard oxidation reduction potential than the metal in an amount of 0.0001 to 10 moles per mole of the cephem compound to obtain the exo-methylenepenam compound

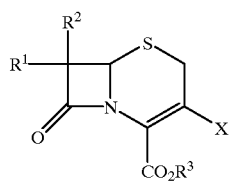

(1)

wherein $R^1$ is a hydrogen atom, amino or protected amino, $R^2$ is a hydrogen atom, halogen atom, lower alkoxyl, lower acyl, lower alkyl, hydroxyl, protected hydroxyl or lower alkyl having hydroxyl or protected hydroxyl as a substituent, $R^3$ is a hydrogen atom or carboxylic acid protective group, X is a halogen atom, lower alkylsulfonyloxy, substituted lower alkylsulfonyloxy, arylsulfonyloxy, substituted arylsulfonyloxy, halogenated sulfonyloxy or substituted halogenated sulfonyloxy

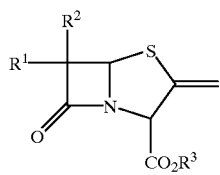

(2)

wherein $R^1$, $R^2$ and $R^3$ are as defined above.

Examples of groups mentioned herein are as follows.

Exemplary of the protected amino represented by $R^1$ are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc.; imido groups such as phthalimido, nitrophthalimido, etc., in addition to the groups disclosed in Theodora W. Greene, 1981, "Protective Groups in Organic Synthesis" (hereinafter referred to merely as the "literature"), Chap. 7 (pp. 218~287). Examples of protective groups for the amino of phenylglycylamido group and p-hydroxyphenylglycylamido group are those disclosed in the literature, Chap. 7 (pp. 218~287). Examples of protective groups for the hydroxyl of p-hydroxyphenylglycylamido group are those disclosed in the literature, Chap.2 (pp. 10~72).

Exemplary of the lower alkoxyl represented by $R^2$ are straight-chain or branched $C_{1-4}$ alkoxyl groups such as methoxy, ethoxy, n-propoxy, isopropoxy, n-butoxy, isobutoxy, sec-butoxy and tert-butoxy groups.

Exemplary of the lower acyl represented by $R^2$ are straight-chain or branched $C_{1-4}$ acyl groups such as formyl, acetyl, propionyl, butyryl and isobutyryl.

Examples of lower alkyl represented by $R^2$ are straight-chain or branched $C_{1-4}$ alkyl group such as methyl, ethyl, n-propyl, isopropyl, n-butyl, isobutyl, sec-butyl or tert-butyl. Examples of protective groups for the protected hydroxyl in the lower alkyl represented by $R^2$ and substituted with hydroxyl or protected hydroxyl, and for the protected hydroxyl represented by $R^2$ are those disclosed in the literature, Chap. 2 (pp. 10~72). The substituted lower alkyl represented by $R^2$ may have as its substituent(s) one or at least two same or different groups selected from among hydroxyl and the protected hydroxyl groups. Such substituent(s) may be positioned on at least one carbon atom of the alkyl.

Exemplary of the carboxylic acid protecting group represented by $R^3$ are allyl, benzyl, p-methoxybenzyl, p-nitrobenzyl, diphenylmethyl, trichloromethyl, tert-butyl, and those disclosed in the literature, Chap. 5 (pp. 152~192).

Examples of halogen atom represented by $R^2$ and X are fluorine, chlorine, bromine or iodine atom.

Examples of lower alkylsulfonyloxy or substituted lower alkylsulfonyloxy are methanesulfonyloxy, trifluoromethanesulfonyloxy and trichloromethanesulfonyloxy. Examples of arylsulfonyloxy or substituted arylsulfonyloxy are benzenesulfonyloxy and toluenesulfonyloxy. Examples of halogenated sulfonyloxy are fluorosulfonyloxy.

The cephem compound represented by the formula (1) for use as a starting material of the present invention can be prepared for example by the following method.

More specifically, as disclosed in JP 49-116,095 A, the compound of the formula (1) is prepared by reacting 3-hydroxycephem compound of the formula (3) with a reactive chlorine compound (phosphorus trichloride, phosphorus oxychloride, etc.) in dimethylformamide.

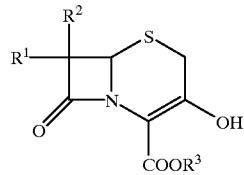

(3)

(wherein $R^1$, $R^2$ and $R^3$ are as defined in above.)

The cephem compound of the formula (1) thus obtained can be converted to an exo-methylenepenam compound of the formula (2) by reacting the compound (1) with a metal having a standard oxidation-reduction potential of up to −0.3 (V/SCE) in an amount of at least one mole per mole of the compound (1) and a metal compound having a higher standard oxidation-reduction potential than the metal in an amount of 0.0001 to 10 moles per mole of the compound (1). V/SCE shows oxidation-reduction potential based on a standard caramel electrode.

More specifically, the reaction is conducted in a suitable solvent. Examples of solvents useful in the reaction are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride, aliphatic hydrocarbons such as pentane, hexane, heptane and octane, cycloalkanes such as cyclopentane, cyclohexane, cycloheptane and cyclooctane, amides such as dimethylformamide and dimethylacetamide, cyclic amides such as N-methylpyrrolidinone, dimethylsulfoxide, etc. These solvents are used singly or in admixture of at least two of them. These solvents may contain water as required. These solvents are used in an amount of about 10 to about 200 liters, preferably about 20 to about 100 liters, per kilogram of the compound of the formula (1). The reaction is conducted usually at −78° C. to 60° C., preferably −40° C. to 30° C. The reaction of the invention proceeds satisfactorily even around room temperature. Further, when required, the reaction can be conducted within a closed container or in an inert gas such as nitrogen gas.

Examples of metals having a standard oxidation-reduction potential of up to −0.3 (V/SCE) are magnesium, aluminum, zinc, iron, nickel, tin, lead, etc., among which magnesium, aluminum, zinc and tin are desirable to use. The shape of these metals is not limited particularly but can be any of a wide variety of forms such as powder, plate, foil, lump and wire. Preferably, the metal to be used is in the form of a powder or foil. The particle size of the powdery metal is preferably about 100 to about 300 mesh although variable over a wide range. These metals are used usually in an amount of about 1 to about 50 moles, preferably about 1 to about 10 moles, per mole of the compound of the formula (1).

Examples of metal compounds having a higher standard oxidation-reduction potential than the above metals are lead compounds (such as lead fluoride, lead chloride, lead bromide, lead iodide and like lead halides, lead nitrate, lead sulfate, lead perchlorate, lead borate, lead carbonate, lead phosphate and like inorganic salts of lead, lead acetate, lead oxalate, lead stearate and like fatty acid salts of lead, lead oxide and lead hydroxide), copper compounds (such as copper fluoride, copper chloride, copper bromide, copper iodide and like copper halides, copper nitrate, copper sulfate, copper perchlorate, copper borate, copper carbonate, copper phosphate and like inorganic salts of copper, and copper oxalate), titanium compounds (such as titanium fluoride, titanium chloride, titanium bromide, titanium iodide and like titanium halides, and titanium nitrate, titanium sulfate and like inorganic salts of titanium), bismuth compounds (such as bismuth fluoride, bismuth chloride, bismuth bromide, bismuth iodide and like bismuth halide, bismuth nitrate, bismuth sulfate and like inorganic salts of bismuth), antimony compounds (such as antimony fluoride, antimony chloride, antimony bromide, antimony iodide and like antimony halides, antimony sulfate and like inorganic salts of antimony, and antimony oxide), and nickel compounds (such as nickel fluoride, nickel chloride, nickel bromide, nickel iodide and like nickel halides, nickel nitrate, nickel sulfate, nickel perchlorate, nickel borate, nickel carbonate, nickel phosphate and like inorganic salts of nickel, nickel acetate and like fatty acid salts of nickel. These metal compounds may be used singly or as a mixture of at least two of them. These metal compounds are used usually in an amount of 0.0001 to 30 moles, preferably 0.001 to 10 moles, per mole of the compound of the general formula (1).

Examples of combinations of metals up to −0.3 (V/SCE) in standard oxidation-reduction potential and metal compounds having a higher standard oxidation-reduction potential are Al/Pb compound, Al/Bi compound, Zn/Pb compound, Zn/Bi compound, Mg/Bi compound, Mg/Cu compound, Sn/Ti compound, Sn/Bi compound, Sn/Sb compound, etc., among which the combinations of Al/Pb compound, Al/Bi compound and Zn/Bi compound are preferred.

It is possible to add an acid to the reaction system in order to proceed the reaction smoothly. Examples of acids are mineral acid such as hydrochloric acid and sulfuric acid, Louis acid such as aluminum chloride.

The exo-methylenepenam derivative of the formula (2) obtained can be isolated by a usual purification procedure.

BEST MODE OF CARRYING OUT THE INVENTION

The present invention will be described below in detail with reference to examples, wherein Ph stands for $C_6H_5$—.

EXAMPLE 1

A 100 mg quantity of compound (1a) ($R^1$=PhCH$_2$CONH, $R^2$=H, $R^3$=CH$_2$C$_6$H$_4$OCH$_3$-p, X=Cl), 14 mg of bismuth chloride, 28 mg of aluminum chloride and 57 mg of aluminum powder were weighed out, placed into a 10-ml egg-plant type flask and stirred at room temperature for 15 hours with addition of 2 ml of N-methyl-2-pyrrolidinone. The reaction mixture was poured into 1N hydrochloric acid and extracted with ethyl acetate. The extract was washed with water twice and then with brine once, and thereafter dried over anhydrous sodium sulfate. The resulting extract was concentrated in vacuo to remove the solvent, and the residue was purified by silica gel column chromatography, giving compound 2a (89 mg, 95%).

$^1$H-NMR (CDCl$_3$) δ: 3.61 (s, 2H), 3.80(s, 3H), 5.11(s, 2H), 5.18(dd, J=1.5, 1.7 Hz, 1H), 5.24(dd, J=1.5, 2.2 Hz, 1H), 5.35(dd, J=1.7, 2.2 Hz, 1H), 5.57(d, J=4.0 Hz, 1H), 5.75(dd, J=4.0, 9.3 Hz, 1H), 6.07(d, J=9.3 Hz, 1H), 6.85~7.40(m, 9H)

EXAMPLE 2

The same reaction as in Example 1 was conducted using, as starting materials, compound (1b) ($R^1$=PhCH$_2$CONH, $R^2$=H, $R^3$=CHPh$_2$, X=Cl), 12 mg of bismuth chloride, 21 mg of aluminum chloride and 49 mg of aluminum powder to obtain the compound 2b (84 mg, 90%).

$^1$H-NMR (CDCl$_3$) δ: 3.61(s, 2H), 5.25(m, 2H), 5.35(m, 1H), 5.59(d, J=4.0 Hz, 1H), 5.75(dd, J=4.0, 8.9 Hz, 1H), 6.12(d, J=8.9 Hz, 1H), 6.84(s, 1H), 7.22~7.40(m, 15H)

EXAMPLE 3

The same reaction as in Example 1 was conducted using, as starting materials, compound (1c) ($R^1$=PhCH$_2$CONH, $R^2$=H, $R^3$=CH$_3$, X=Cl), 16 mg of bismuth chloride, 36 mg of aluminum chloride and 74 mg of aluminum powder to obtain the compound 2c (81 mg, 89%).

$^1$H-NMR (CDCl$_3$) δ: 3.63(ABq, J=2.7 Hz, 2H), 3.78(s, 3H), 5.19(dd, J=1.9, 1.9 Hz, 1H), 5.28(dd, J=1.9, 1.9 Hz, 1H), 5.40(dd, J=1.9, 1.9 Hz, 1H), 5.60(d, J=4.0 Hz, 1H), 5.77(dd, J=4.0, 8.8 Hz, 1H), 6.20(d, J=8.8 Hz, 1H), 7.27–7.37(m, 5H)

EXAMPLE 4

The same reaction as in Example 1 was conducted using, as starting materials, compound (1d) ($R^1$=PhCH$_2$CONH, $R^2$=H, $R^3$=CH$_2$C$_6$H$_4$OCH$_3$-p, X=OSO$_2$CF$_3$), 59 mg of bismuth chloride, 25 mg of aluminum chloride and 46 mg of aluminum powder to obtain the compound 2a (71 mg, 95%). The resulting compound was fully identical with that of Example 1 in spectral data.

EXAMPLE 5

The same reaction as in Example 1 was conducted using, as starting materials, compound (1e) ($R^1$=PhCH$_2$CONH, $R^2$=H, $R^3$=CHPH$_2$, X=OSO$_2$CF$_3$), 54 mg of bismuth chloride, 23 mg of aluminum chloride and 43 mg of aluminum powder to obtain the compound 2b (69 mg, 90%). The resulting compound was fully identical with that of Example 2 in spectral data.

EXAMPLE 6

The same reaction as in Example 1 was conducted using, as starting materials, compound (1f) ($R^1$=PhCH$_2$CONH, $R^2$=H, $R^3$=CH$_2$C$_6$H$_4$OCH$_3$-p, X=OSO$_2$C6H$_4$—CH$_3$-p), 62 mg of bismuth chloride, 26 mg of aluminum chloride and 44 mg of aluminum powder to obtain the compound 2a (54 mg, 75%). The resulting compound was fully identical with that of Example 1 in spectral data.

EXAMPLES 7 TO 9

The same reaction as in Example 1 was performed using the following metal compound. Table 1 shows the result.

TABLE 1

| Example | metal compound | yield (%) |
|---|---|---|
| 7 | BiCl$_3$(7)/AlCl$_3$(28) | 90 |
| 8 | BiCl$_3$(70)/AlCl$_3$(28) | 93 |
| 9 | PbBr$_3$(16)/AlCl$_3$(28) | 89 |

EXAMPLES 10 TO 12

The same reaction as in Example 1 was performed using the following solvents. Table 2 shows the result.

TABLE 2

| Example | solvent | yield (%) |
|---|---|---|
| 10 | DMF | 85 |
| 11 | DMI | 83 |
| 12 | THF | 72 |

DMI: dimethylimidazolizinone

Reference Example

Bioorganic and Medicinal Chemistry Letters, 3, 2253 (1993) discloses a process for preparing a penem compound having β-lactamase inhibitory activity, from exo-methylenepenam (2b) obtained by the present invention and serving as a starting material. This process generally comprises the following steps. An exo-methylenepenam compound (A) is decomposed by ozonolysis into a ketone (B), which is then reacted in the presence of trifluoromethanesulfonyl anhydride and a base to obtain an enoltriflate (C). This compound is reacted with various thiols (RSH) to derive a penem compound (D). The compound is deprotected and purified, affording a compound (E) having β-lactamase inhibitory activity.

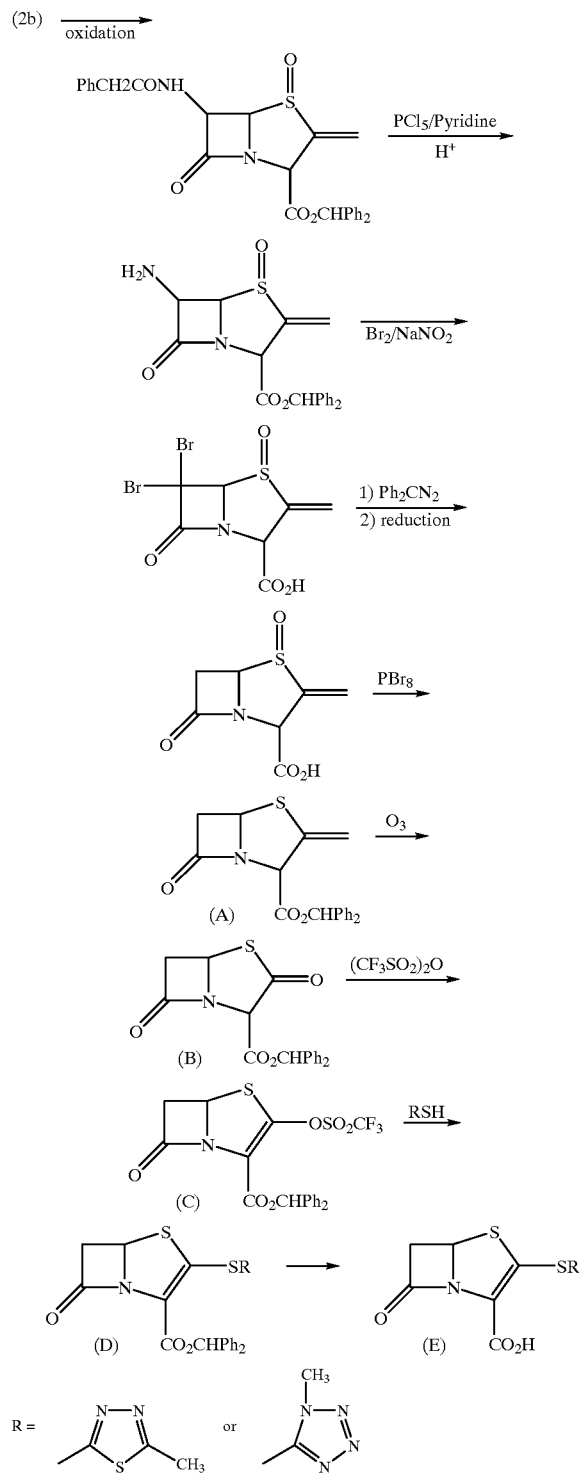

INDUSTRIAL APPLICABILITY

According to the present invention, an exo-methylenepenam compound of the formula (2), which is an important intermediate for synthesizing, for example, a β-lactamase inhibitor, can be prepared from the cephem compound of the formula (1) serving as a starting material in a high yield with a high purity through a safe and simplified procedure.

What is claimed is:

1. A process for preparing an exo-methylenepenam compound represented by the formula (2) wherein cephem compound represented by the formula (1) is reduced with (a) a metal having a standard oxidation-reduction potential of up to −0.3 (V/SCE), said metal being in an amount of at least one mole per mole of the cephem compound, and with (b) a metal compound having a higher standard oxidation reduction potential than the metal, said metal compound being present in an amount of 0.001 to 10 moles per mole of the cephem compound, and said metal compound being at least one member selected from the group consisting of halide, inorganic acid salt, fatty acid salt, oxide, and hydroxide of lead, copper, titanium, bismuth, antimony and nickel to obtain the exo-methylenepenam compound

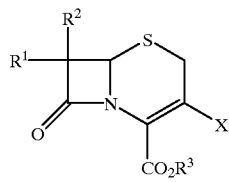

(1)

wherein $R^1$ is a hydrogen atom, amino or protected amino, $R^2$ is a hydrogen atom, halogen atom, lower alkoxyl, straight-chain or branched $C_{1-4}$ acyl group selected from the group consisting of formyl, acetyl, propionyl, butyryl or isobutyryl, lower alkyl, hydroxyl, protected hydroxyl or lower alkyl having hydroxyl or protected hydroxyl as a substituent, $R^3$ is a hydrogen atom or carboxylic acid protective group, X is a halogen atom, lower alkylsulfonyloxy, trifluoromethanesulfonyloxy, trichloromethanesulfonyloxy, arylsulfonyloxy, toluenesulfonyloxy, or halogenated sulfonyloxy

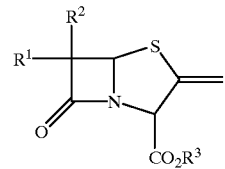

(2)

wherein $R^1$, $R^2$ and $R^3$ are as defined above.

2. A process as defined in claim 1 wherein the metal is magnesium, aluminum, zinc, iron, nickel, tin or lead.

3. A process as defined in claim 1 wherein the metal compound is lead compound, copper compound, titanium compound, bismuth compound, antimony compound or nickel compound.

4. A process as defined in claim 1 wherein the combination of metal and metal compound is Al/Pb compound, Al/Bi compound, Zn/Pb compound, Zn/Bi compound, Mg/Bi compound, Mg/Cu compound, Sn/Ti compound, Sn/Bi compound or Sn/Sb compound.

* * * * *